United States Patent [19]

Canie

[11] 4,306,549

[45] Dec. 22, 1981

[54] SPLINT-CAST

[76] Inventor: Joseph G. Canie, P.O. Box 1021, Timmins, Ontario, Canada, P4N 7H6

[21] Appl. No.: 48,714

[22] Filed: Jun. 15, 1979

Related U.S. Application Data

[63] Continuation-in-part of Ser. No. 8,262, Feb. 1, 1979, abandoned.

[51] Int. Cl.³ ............................................... A61F 5/04
[52] U.S. Cl. ..................................... 128/90; 264/102; 264/222
[58] Field of Search ............... 128/89 R, 90, 165, 169, 128/DIG. 6, 77, 83, 595; 3/36; 264/102, 571, 222, 223, DIG. 30

[56] References Cited

U.S. PATENT DOCUMENTS

| | | | |
|---|---|---|---|
| 2,903,389 | 9/1959 | Fujita | 264/102 |
| 3,048,169 | 8/1962 | Pierce | 128/90 |
| 3,059,636 | 10/1962 | Schwartz | 128/DIG. 6 |
| 3,110,307 | 11/1963 | Hamilton | 128/89 R |
| 3,121,430 | 2/1964 | O'Reilly | 128/595 |
| 3,373,741 | 3/1968 | Hill et al. | 128/90 |
| 3,415,243 | 12/1968 | Sheldon | 128/90 |
| 3,674,021 | 7/1972 | Snyder et al. | 128/90 |
| 3,680,549 | 8/1972 | Lehneis et al. | 128/89 R |
| 3,782,390 | 1/1974 | Johnson | 264/222 |
| 3,919,724 | 11/1975 | Sanders et al. | 3/36 |
| 4,006,741 | 2/1977 | Arluck | 128/89 R |
| 4,019,506 | 4/1977 | Eschmann | 128/90 |
| 4,193,395 | 3/1980 | Gruber | 128/90 |

FOREIGN PATENT DOCUMENTS

| | | | |
|---|---|---|---|
| 1954070 | 4/1971 | Fed. Rep. of Germany | 264/102 |
| 2616291 | 11/1977 | Fed. Rep. of Germany | 128/90 |
| 1451929 | 7/1966 | France | 264/102 |

Primary Examiner—Robert W. Michell
Assistant Examiner—Arthur S. Rose
Attorney, Agent, or Firm—Larson and Taylor

[57] ABSTRACT

The novel splint-cast, before use, is a longitudinally flexible strip consisting of fibreglass reinforcing mat overlying and sealed adjacent an insulating layer at least partially by a non-permeable wrap material. On the other side of the insulating layer is a liner material of preferably a wool/cotton composition. The splint-cast blank may be prepared for use by passing a curable hardening agent into a vacuumed envelope formed by the wrap and the insulating material or the wrap and a latex layer, the fibreglass reinforcing mat absorbing the hardening agent along the length of the splint-cast blank. Before the hardening agent sets, the splint-cast is applied to an injured limb as a bandage but with consecutive wrappings about the limb in spaced relationship to each other. The splint-cast is simple and convenient to both prepare for use and apply. The open wrapping nature of the splint-cast on an injured limb permits air circulation while also providing desired firm support.

18 Claims, 6 Drawing Figures

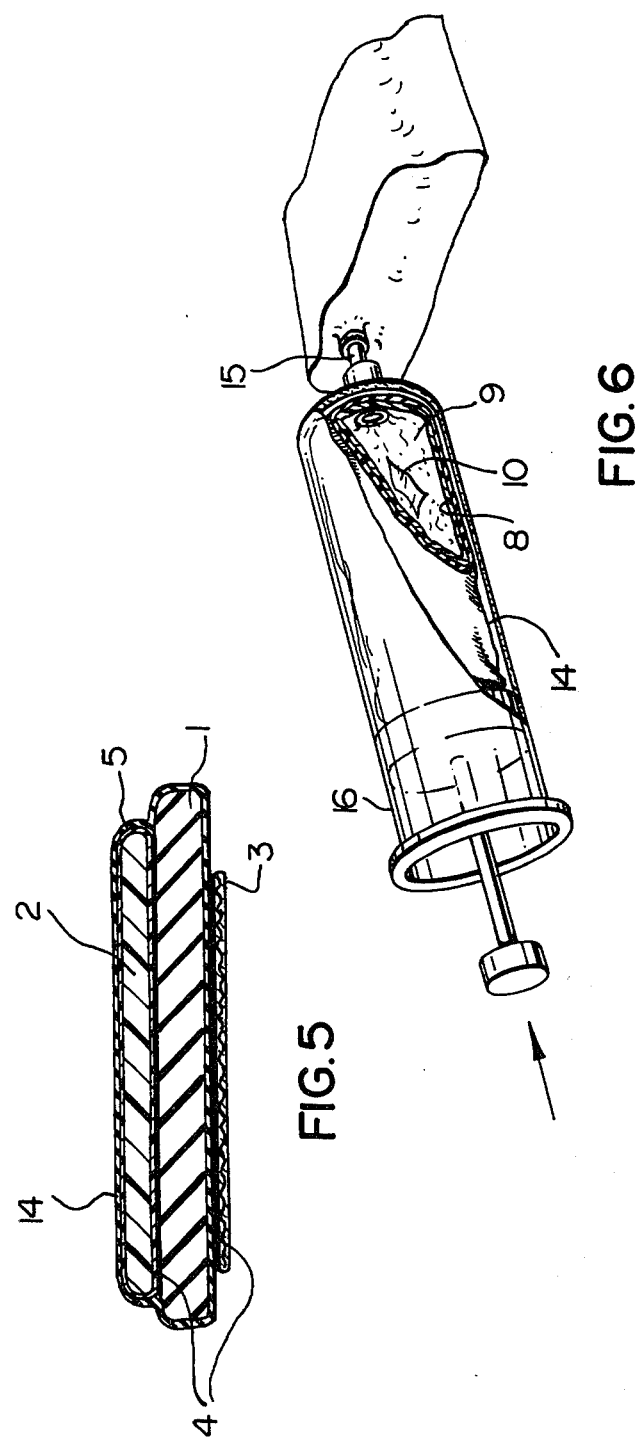

SPLINT-CAST

CROSS-REFERENCES TO RELATED APPLICATIONS

This application is a continuation-in-part of application Ser. No. 8,262, filed Feb. 1, 1979, now abandoned.

BACKGROUND OF THE INVENTION

Present known methods of immobilizing broken, fractured, sprained or strained limbs during the curing period generally consist of plaster-of-paris casts which are applied in a closed configuration, i.e. the cast encloses the whole of the limb except at the ends where a hand or foot may protrude and an opposed end where an upper portion of the limb passes into the cast.

However, this conventional method of supporting an injured limb has several drawbacks. Application of the cast requires skilled and trained personnel to apply the wet slurry to the limb over a stockinette or other similar gauze-type material, a task which generally takes about 15 to 45 minutes. A particular disadvantage is that, should the patient's skin be lacerated and broken, healing of the skin is either very difficult or prevented. Obviously, this can cause pain and general soreness to the patient. However, and perhaps more importantly, as the plaster-of-paris cast dries and cures, so heat is generated and much of this heat is passed to the patient's limb. This causes swelling of the damaged limb which tightens within the cast, blood circulation is affected which can cause further swelling leading to further blood circulatory problems. Thus, the swelling which frequently accompanies a skeletal fracture or break, torn ligaments, etc. is increased by the application of heat thereto from the setting cast.

The application of cold water or ice directly to the cast at this stage is not possible since the cast would disintegrate. Furthermore, such cooling treatment is not practicable at any time since the cast is not waterproof or resistant to deterioration by water. After the heat from the cast has eventually dissipated, swelling of the limb may subside but the closed nature of the cast about the limb prevents air-circulation and bathing of the limb. The latter is a very real problem for patients wearing a cast for several weeks.

Furthermore, the plaster-of-paris cast takes approximately 5-15 minutes to set, after which time the cast can still be displaced by movement of the patient. It is not until the cast has fully cured, which takes about 48 hours, that the cast is fully hardened, by which time it may have been displaced and rendered far from functional.

Additionally, if the plaster-of-paris cast is to be a walking cast, it must be modified by the application of a solid, bulky plaster portion under the foot. This of course requires the usual 48 hours before it has cured and can be used for walking. The portion under the foot also means that the leg with the cast is effectively longer than the other leg.

Removal of the traditional plaster-of paris cast whilst not being a very difficult problem necessitates a somewhat dirty and time consuming cutting operation. Furthermore, damage to the limb is possible when the cast is broken away.

Refinements on the traditional plaster-of-paris cast have been attempted from time to time, none of them having been particularly successful or used to any great extent. U.S. Pat. No. 3,110,307 to Hamilton, teaches a flexible solid body which is partitioned for receiving a pre-mixed hardening material. In use, metal end caps are fitted to the solid body splint and the pre-mixed material is forced in along longitudinal compartments. The solid body is then fitted to the limb of a patient and, the end caps optionally removed after the hardening agent has cured. However, this splint incorporates most of the disadvantages of the conventional plaster-of-paris cast. Principally, it has the closed cast configuration which prevents air-circulation and bathing of the encased limb. Again, much of the heat generated by the curing hardening agent is imparted to the encased limb to cause swelling and associated blood circulatory problems.

U.S. Pat. No. 3,415,243 to Sheldon utilizes a strip or bandage type cast which is applied to the injured limb in a traditional bandage configuration before a hardening material within the strip cures. The cast has the disadvantage that possibly toxic hardening reagents could contact the skin due to the open-sided or sandwich configuration of the strip. Furthermore, the cured cast, in traditional manner, totally encloses the injured limb thereby reducing air-circulation and creating heat dissipation and blood circulatory problems.

It is an object of the present invention to provide a splint or cast which effectively immobilizes an injured limb, and which can be simply, speedily and cleanly applied.

A further object of the invention is to provide a splint or cast when dissipates heat outwards away from the patient's limb thereby reducing swelling and blood circulatory problems.

Yet another object of the present invention is to provide a splint or cast which can be applied to an injured limb in an open-cast or non-total enclosure configuration with spacing between successive wrappings or windings of the product around an injured limb whilst at the same time providing effective support. This permits air circulation about the injured limb and associated improved skin care.

Still, a further object of the present invention is to provide a product which will withstand wetting during bathing.

SUMMARY OF THE INVENTION

According to the present invention, there is now provided a splint-cast blank comprising a strip of heat insulating material having longitudinal flexibility and a substantially flat transverse form, strengthening means adjacent one face of the heat insulating material and held within a vacuumed envelope at least partially by a wrap sheet of flexible substantially gas impermeable material which is heat sealed to itself and/or the insulating material and a liner adjacent a face of the insulating material which is opposed to said one face, said splint-cast blank excluding the liner being waterproof and resistant to deterioration by water.

In another aspect, the invention also provides a splint-cast formed of a rigid, composite strip having an open spiral intermediate portion with terminal portions inside the spiral, the composite strip comprising rigid, water-resistant layers attached to a water-resistant heat insulating layer which is on the inside of the spiral, the rigidity and configuration of the splint being such as to resist twist about the axis of the spiral, and being such as to resist compression along the axis of the spiral.

Furthermore, there is provided a splint-cast pack for preparation of a splint-cast blank immediately prior to application to an injured limb, said pack including a splint-cast blank which comprises a strip of heat insulating material having longitudinal flexibility and a substantially flat transverse form, strengthening means adjacent one face of the heat insulating material and held within a vacuumed envelope at least partially by a wrap sheet of flexible substantially gas impermeable material which is heat sealed to itself and/or the insulating material, a liner adjacent a face of the heat insulating material which is opposed to said one face, and a valve in communication with said envelope said valve permitting the passage of a fluid hardening agent into the envelope, said splint-cast blank excluding the liner being waterproof and resistant to deterioration by water, the pack also including a hardening agent dispenser unit containing a hardening agent, the dispenser unit being attachable to said valve for directing said hardening agent into said envelope.

The present invention also includes a method of preparing a splint-cast blank as hereinbefore defined disposing a first terminal portion of the splint-cast blank in a substantially straight line along a patient's limb; winding an intermediate portion of the blank about said limb over said first terminal portion to form said open spiral of the splint-cast; tucking a second terminal portion of the blank under an adjacent winding of said intermediate portion; and permitting the hardening agent to cure.

The wrap sheet may be heat sealed to the heat insulating material which is preferably blown synthetic rubber having a non-cellular skin. The strengthening means, which is preferably woven fibreglass mat, is disposed within the vacuumed envelope defined by the wrapped sheet and one face of the heat insulating material.

Alternatively the wrap sheet may substantially enclose the strengthening means, the whole then being attached to the heat insulating material. A layer of latex material preferably surrounds the wrapped strengthening means and heat insulating material to form a gas impermeable seal therearound.

Furthermore, preferably a valve is attached to the woven fibreglass mat strengthening means prior to application of the wrap sheet and the latex. When manufacturing the splint-cast blank, the valve thus positioned is utilized to withdraw air from the space in which the strengthening means is enclosed. If desired, the wrap sheet, strengthening means and heat insulating material is cold dipped in latex solution, the partially formed splint-cast blank being held by the protruding valve. The latex on the blank is then cured after which the blank may be passed to a probe for evacuation of air from the envelope retaining the fibreglass mat.

When preparing the splint-cast blank in the field, a curable hardening agent is passed into the vacuumed envelope, the woven fibreglass mat readily soaking up the curable hardening agent which then cures within a predetermined time. Prior to curing, the splint-cast is applied to an injured limb so that the hardening agent cures to form a supporting splint or cast.

A dispenser unit for injecting the hardening reagent into the splint-cast blank consists of a flexible, preferably transparent, bag containing uncatalyzed hardening agent and a capsule with catalyst. The capsule may be burst by finger pressure and the flexible dispenser bag kneaded in order to mix the catalyst with the hardening agent. The dispenser bag contains a probe or nozzle which is receivable by the nozzle of the splint-cast blank. Preferably, the dispenser bag is placed inside a syringe so that the probe or nozzle of the dispenser bag protrudes from the syringe tip. The syringe may then be used to inject the curable hardening reagent into the splint-cast blank and reused for subsequent loading or injecting operations. In order to ensure a good seal for the flexible dispenser bag which is preferably formed of plastics material, the dispenser bag is cold dipped in latex. Allergic reactions are thus minimized by the latex outer layer on both the dispenser bag and the splint-cast blank. The latex provides an additional advantage in that the vacuum in the envelope is maintained and prevention of leakage from the dispenser bag is assured.

The spling-cast blank may be formed having a thickness of approximately 5/16 inch in a preferred embodiment.

BRIEF DESCRIPTION OF THE DRAWINGS

FIG. 5 is a cross-section of another embodiment of the heat-insulated splint-cast blank; and FIG. 6 illustrates a portion of the splint-cast blank according to FIG. 5 which is temporarily connected to a dispenser unit.

DESCRIPTION OF THE PREFERRED EMBODIMENT

Figure 1:
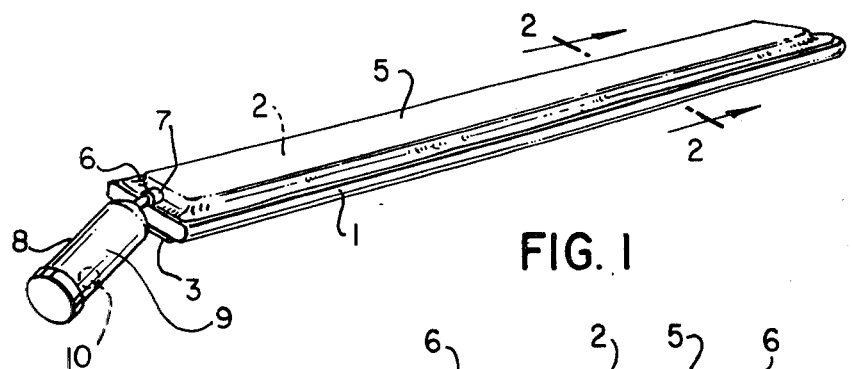
FIG. 1 in a perspective view of a portion of a splint-cast blank according to the present invention which is temporarily connected to a hardening agent dispenser unit.
Figure 2:
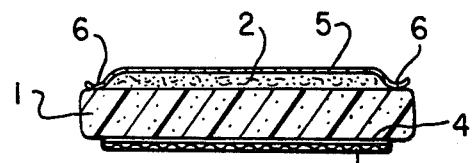
FIG. 2 is a cross-section of the heat-insulated splint-cast blank before preparation for use.

The splint-cast includes an insulation layer 1 sandwiched between glass fibre reinforcing mat 2 and a liner material 3 which is preferably attached to the insulation layer 1 by a glue layer 4. The glass mat 2 is held onto the insulation 1 by a wrap 5 which is heat sealed at its end and edges 6 to the insulation 1.

The wrap 5 thus forms an envelope in which the fibreglass mat 2 is tightly enclosed. The wrap material should be substantially non-permeable to gases and of a material which can be heat sealed to the insulation 1. It is applied to the insulation 1 over the mat 2 by a conventional heat sealing process used in the vacuum packaging art. Air is evacuated from the envelope during an end sealing step to leave the fibreglass mat 2 in a vacuum.

A convenient material for the wrap 5 is that at present used in food packaging which desirably readily conforms to the shape of the fibreglass mat during vacuum formation. However, the principal requirement for the wrap material is that it be substantially non-gas permeable.

The fibreglass web is approximately $\frac{1}{8}$ of an inch thick. It may conveniently be formed by several layers of mat. Preferably, woven mat is used since this reduces the likelihood of stray glass fibres protruding sideways on the insulation material and preventing the formation of an effective heat seal between the wrap and the insulation.

The insulation material is formed of a flexible foam having a non-cellular skin such as neoprene and latex foams. Other synthetic foams such as polyethylene or polyurethane foam may also be used in certain instances. It is important that the insulation material be of sufficient thickness to act as an adequate heat insulator during curing. Thus, while the insulation desirably provides comfort, it is important that the insulation functions to prevent heat conduction to the liner when a hardening agent in the envelope is curing.

The heat insulating material may be extruded in the desired shape and then cut to a desired length. The density of the extruded synthetic foam rubber is controlled with hydrogen gas in order to give a desired compressibility and weight.

The liner 3 is a wool-cotton composition and it permits the skin in contact therewith to breath. The liner may be initially sprayed on one side with a silicone resin coating and glued to the underside of the insulation 1, the silicone coating providing a glue receptive layer on the liner 3 and preventing glue being absorbed by the liner 3.

A plastic vinyl valve 7 is attached to the splint-cast blank in the end of the envelope defined between the wrap 5 and the insulation 1 and permits hardening agent to pass into the envelope. For this purpose, a dispenser 8 holding a hardening agent 9, such as polyester resin with catalyst 10 is connected to the valve 7. The hardening agent 9 readily passes into the evacuated envelope with the fibreglass mat 2 soaking up the agent and transmitting it along the length of the splint-cast blank. Gentle hand pressure from an operator assists in spreading the hardening agent 9 within the envelope.

The valve 7 is preferably installed during the wrap 5 heat sealing operation when an end of the wrap 5 is sealed around the valve 7 which is disposed on the insulation 1. Care is taken to ensure that the valve 7 is sealed around its edges. Finally, the opposite wrap end is heat sealed as vacuum is applied to the envelope. The valve is a liquid valve and thus does not permit air to pass during the vacuum operation. However, it does permit a liquid hardening agent to pass therethrough into the envelope when a greater than atmospheric pressure is applied, i.e., more than 15 p.s.i. Alternatively, the valve can incorporate a membrane which must be pierced by the dispenser 8 before the hardening agent can pass into the envelope. After the splint-cast blank has been applied to a limb and the hardening agent has cured, for convenience, the valve 7 can simply be cut off flush with the wrap 5.

The dispenser 8 carries the catalyst or curing agent together with a colouring agent in a capsule 10 which is readily broken by finger pressure from outside the dispenser 8 in order to mix with the hardening agent 9 immediately prior to injection into the splint-cast. The colouring agent enables an operator to know when the catalyst is adequately mixed. After injection, the dispenser 8 is withdrawn and the splint-cast is ready for application to a patient's limb.

Figure 3:
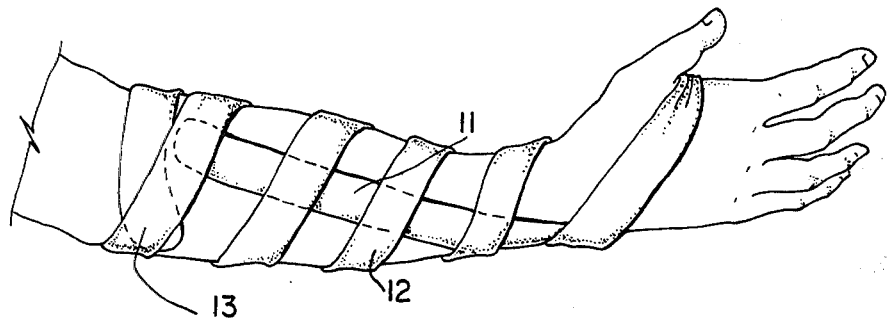
FIG. 3 illustrates the manner of application of the splint-cast to a patient's injured arm.
Figure 4:
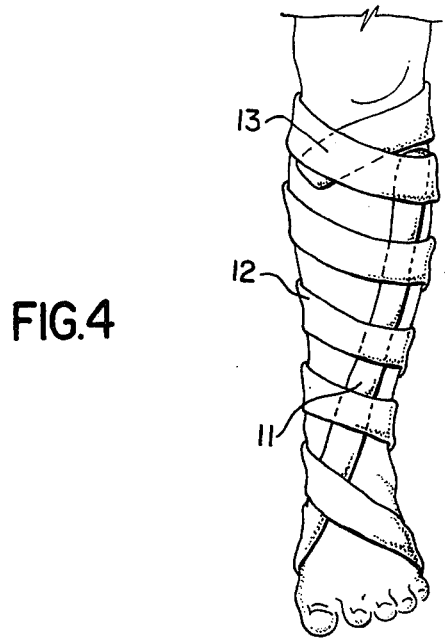
FIG. 4 illustrates the manner of application of the splint-cast to a patient's injured leg.

FIGS. 3 and 4 illustrate preferred splint-cast configurations for a human arm and a human leg. An end 11 of the prepared splint-cast blank, i.e. with hardening agent, is initially placed in a generally straight line along the limb and then around the hand or foot before an intermediate section 12 of the blank is wound around the limb over the generally straight end of the blank. Finally, the other end 13 of the blank is tucked under a winding and the hardening agent within the blank permitted to cure whereafter the splint-cast immobilizes the limb. Modifications of these preferred configurations are obviously possible within the present invention for different types of fracture, etc.

FIG. 5 illustrates another preferred embodiment of the splint-cast blank. In this embodiment, latex rubber encapsulates the wrap 5, woven fibreglass mat 2 and heat insulation layer 1. Furthermore, the woven fibreglass mat 2 is wrapped within the wrap 5 prior to attachment, which may be by means of glue, to one face of the insulation layer 1. The wrap material, as well as being substantially non-permeable to gases, is preferably any thin, light-weight material having a "cling" property, such as those materials sold under the trade marks SARAN WRAP and STRETCH-N-SEAL. The heat insulating material need not have a non-cellular skin in this embodiment since the wrap 5 which surrounds the fibreglass mat 2 prevents hardening agent from becoming absorbed into the insulation layer 1.

The principal feature of the embodiment of FIG. 5 is that the non-allergenic latex layer 14 totally surrounds all parts of the splint-cast blank excluding the liner 3. A small valve 7 has a flattened end and is stitched or otherwise attached to an end portion of the woven fibreglass strip. The valve 7 may have a somewhat elongated opposed receiving end protruding from the splint-cast blank for receiving a locating probe of a dispenser unit.

In order to prepare the splint-cast blank according to the embodiment of FIG. 5, the valve 7 is stitched or otherwise attached to an end portion of the woven fibreglass mat 2 at its flattened end thereof. The wrap 5 is then wrapped around the fibreglass mat 2 and preferably heat sealed along the long side of the wrap. Ends of the strip may not be sealed but this is relatively unimportant since one of the following stages in the preparation of the splint-cast blank seals the ends. The wrapped fibreglass mat 2 with valve 7 is then attached to one face of an extruded foam rubber strip 1 and the composite unit is then cold dipped perhaps a half a dozen times or more in liquid latex which may be coloured. This dipping seals the ends of the wrapped fibreglass mat 2 thus ensuring a gas impermeable envelope in which the fibreglass mat is disposed. The blank, with uncured covering of latex, is then passed to an oven at about 140° to 200° C. for about 1 to 3 hours. Any type of curing oven may be used, for example, a micro-wave oven. The blank is then passed to a probe which is passed into the valve 7 and air is then evacuated from the woven-fibreglass mat and surrounding spaces in the envelope. A layer of glue 4 is then placed over one side of the partially formed blank and a wool/cotton liner 3 is then attached. Latex is of course preferable to other covering materials because it is 100% gas impermeable and causes no allergenic reactions on the skin.

FIG. 6 illustrates the dispenser unit which consists of a bag 8 of flexible, transparent plastics material which is filled with hardening agent 9 such as polyester resin. The dispenser bag 8 also holds a small, flexible and burstable capsule 10 which contains a catalyst for the hardening agent. A nozzle or probe 15 is heat-sealed or otherwise attached to the dispenser bag 8 as the latter is heat sealed during a closing operation. The dispenser bag, with nozzle protruding therethrough, is then cold dipped in transparent latex in order to ensure a strong seal.

In order to dispense the curable resin material into the splint-cast blank, the capsule containing catalyst is firstly broken or bust by finger pressure and the catalyst mixed with the resin by kneading the dispenser bag 8 until an operator can see that the resin and catalyst are thoroughly mixed. The dispenser bag 8 is then placed inside a syringe 16, the probe or nozzle of the dispenser bag protruding through the tip of the syringe. The probe is then opened, aligned and placed into the valve 7 of the splint-cast blank and the syringe is then operated in conventional manner in order to dispense the curable resin material into the splint-cast blank. When the curable resin is fully injected into the blank, the syringe 16, complete with dispenser bag 8 and probe 15, is withdrawn from the valve 7. The empty dispenser bag 8 is then removed from the syringe 16 and discarded, the syringe being reuseable for subsequent splint-cast blank filling operations.

In yet an alternative embodiment of the dispenser unit, the dispenser bag 8 with latex 14 contains only hardening agent 9 but no catalyst capsule 10. Instead the catalyst may be supplied in a separate ampule and injected into the dispenser bag 8 through a valve means, preferably a rubber plug, which is disposed in a wall of the dispenser bag 8. The dispenser bag is then kneaded to mix the catalyst and hardening agent as described above.

This arrangement provides the facility for selecting desired amount of catalyst (in an appropriately labelled ampule) for controlling the curing time of the hardening agent. Obviously this control over setting time of the splint-cast gives more versatility and adaptability for the splint-cast applied for different injuries. Furthermore, the provision of a splint-cast pack in which different sized ampules of catalyst are supplied in a manner separated from the dispenser bag improves shelf-life.

Since the splint-cast attains 90% of maximum strength within a matter of minutes, displacement problems which are associated with conventional casts are avoided. Application of the splint-cast takes only 15 to 30 seconds in contrast to the plaster-of-paris cast which takes 15 to 45 minutes to apply.

The manner in which the splint-cast blank is applied to the injured limb is new since it is wrapped around the limb in a manner which permits approximately 30-60% of the skin area of the limb to be exposed. Thus, contact with lacerations of the skin can be avoided. Furthermore, the open cast or non-total enclosure arrangement reduces the possibilities of a skin reaction with the splint-cast. Lightness of the splint is also greatly increased. The splint is easily removed from the limb by simply sawing through one of the turns of the set splint-cast.

If the splint-cast is applied to the leg and under the foot, it can be used without modification as a walking cast within minutes since the hardening agent has cured by this time and 90% maximum strength has been attained.

The splint-cast blank may be conveniently manufactured in any desired length for different sized limbs. Furthermore, the splint-cast may be supplied in various widths.

Although the splint-cast blank can be very readily applied and removed by relatively unskilled personnel, it is very durable and can remain on a patient's limb for longer periods of time than conventional casts without deterioration. The open-cast and water proof nature of the splint-cast permits a patient to regularly bathe the limb as desired without damage to the supportive and immobilizing nature of the splint-cast and may be conveniently blow dried to speed up drying.

What I claim is:

1. A splint cast formed of a rigid, composite elongated strip having a first and second terminal portions, said first terminal portion being disposed in a substantially straight line and adapted to lie along a patient's limb, said strip having a portion intermediate said first and second terminal portions, said intermediate portion being formed as a spiral adapted to fit securely around a portion of a living being, said spiral having a plurality of turns enveloping said first terminal portion, said turns being spaced longitudinally in order to provide intermediate open spaces, said first terminal portion being tucked underneath a plurality of said turns of said intermediate portion, the composite strip comprising a rigid, water resistant layer attached to a water-resistant heat insulating layer which is on the inside of the spiral, the rigidity and configuration of the splint being such as to resist twist about the axis of the spiral, and being such as to resist compression along the axis of the spiral.

2. A splint-cast according to claim 1 wherein the rigid, water-resistant layer include a wrap sheet overlying a rigid fibreglass layer, the wrap sheet being heat sealed at peripheral portions to said heat insulating layer.

3. A splint-cast according to claim 1 or 2 further comprising a liner attached to an inside face of the heat insulating layer.

4. A splint cast according to claim 3 wherein said liner has a silicone resin coating which is glued to the heat insulating layer thereby attaching said liner thereto.

5. A splint-cast according to claim 1 wherein the rigid, water-resistant layer include a wrap sheet substantially surrounding a rigid fibreglass layer, the wrap sheet being heat sealed onto itself along at least one edge.

6. A splint-cast according to claim 1 further comprising a latex layer sealing surrounding said water-resistant layer and said heat insulating layer.

7. A splint-cast according to claim 6 further comprising a liner attached to an inside face of the latex.

8. A splint cast according to claim 1 wherein said rigid water resistant layer comprises a woven fiber glass mat and a cured hardening agent.

9. A splint cast according to claim 1 wherein said heat insulating layer comprises a material having a non cellular skin.

10. A method of providing a splint cast on a patient's limb, said splint cast comprising an elongate hardenable splint cast blank having first and second terminal portions and a portion intermediate said first and second terminal portions, said blank comprising a hardenable water resistant layer attached to a water resistant heat insulating layer, said method comprising: disposing a first terminal portion of said splint cast blank in a substantially straight line along a patient's limb; winding said intermediate portion as a spiral around the patient's limb such that the spiral has a plurality of turns enveloping the patient's limb and said first terminal portion and such that said heat insulating layer is on the inside of said spiral, said turns being spaced longitudinally in order to provide intermediate open spaces, said first terminal portion lying underneath a plurality of said turns of said intermediate portion; securing said second terminal portion to at least one of said turns of said intermediate portion; and hardening the hardenable water resistant layer to form a rigid splint cast on the patient's limb, the rigidity and spiral configuration of the splint being such as to resist twist about the axis of the spiral, and being such as to resist compression along the axis of the spiral.

11. A method according to claim 10 wherein said hardenable water resistant layer comprises strengthening means adjacent one face of the heat insulating layer and held within an envelope at least partially by a wrap sheet of flexible substantially gas impermeable material secured to said heat insulating material.

12. A method according to claim 11 comprising, prior to disposing said first terminal portion of said splint cast on a patient's limb, introducing a fluid hardening agent into said envelope to saturate said strengthening means.

13. A method according to claim 12 wherein said strengthening means comprises woven fiber glass mat.

14. A method according to claim 13 wherein said envelope is evacuated and comprises a valve for admitting said fluid hardening agent into the vacuumed envelope.

15. A method according to claim 14 wherein said fluid hardening agent comprises a curable epoxy or polyester resin.

16. A method according to claim 14 wherein said hardening agent is admitted into said envelope from a dispenser unit, said dispenser unit being attachable to said valve for directing said hardening agent into said envelope.

17. A method according to claim 16 wherein said dispenser unit comprises a catalyst capsule, said capsule containing a catalyst for hardening agent in said dispenser unit and being breakable by external finger pressure on the dispenser unit.

18. A method according to claim 10 wherein said step of securing said second terminal portion comprises tucking said second terminal portion underneath a turn of said intermediate portion.

* * * * *